United States Patent [19]

Hozier

[11] Patent Number: 5,563,060
[45] Date of Patent: *Oct. 8, 1996

[54] MICRO-LIBRARIES FOR SCREENING CELL POPULATIONS

[76] Inventor: John Hozier, 8950 S. Tropical Trail, Merritt Island, Fla. 32952

[*] Notice: The term of this patent shall not extend beyond the expiration date of Pat. No. 5,326,691.

[21] Appl. No.: 231,186

[22] Filed: Apr. 22, 1994

Related U.S. Application Data

[62] Division of Ser. No. 795,462, Nov. 21, 1991.

[51] Int. Cl.$^6$ ............................. C12N 5/04; C12N 5/06; C12N 1/19; C12N 1/21
[52] U.S. Cl. ................ 435/240.23; 435/240.4; 435/252.33; 435/254.22
[58] Field of Search ..................... 935/77, 78, 79; 435/6, 7.2, 30, 240.33, 243, 240.4, 252.8, 254.2, 252.33, 240.23, 91.2

[56] References Cited

U.S. PATENT DOCUMENTS

| | | | |
|---|---|---|---|
| 5,061,621 | 10/1991 | Periman | 435/30 |
| 5,326,691 | 6/1994 | Hozier | 435/6 |

OTHER PUBLICATIONS

Uber (1994) "Robotics and the human genome project" Bio/Technology 12:80–81.
Nizetic et al. (1991) "Construction, arraying, and high–density screening of large insert libraries of human chromosomes X and 21: Theripotential use as reference libraries" Proc. Natl. Acad. Sci. USA 88:3233–3237.
Drmanac et al. (1992) "Sequencing by hybridization: Towards an automated sequencing of one million M13 clones arrayed on membranes" Electrophoresis 13:566–573.
Banchereau et al., "Growing Human B Lymphocytes in the CD40 System", *Nature* 353: (1991) pp. 678–679.
Mendez et al., "Rapid Screening of a YAC Library by Pulsed–Field Gel Southern Blot Analysis of Pooled YAC Clones", (1991) *Genomics* 10: 661≅665.
Helmstetter et al., "Mechanism for Chromosome and Minichromosome Segretations in *Escherichia coli.*", (1987) *J. Mol. Biol.* 197: 195–204.
Lennon et al., "Hybridization Analyses of Arrayed cDNA Libraries", (1991) *Trends in Genetics* 7:314–317.

Neidhardt et al, Chapter 14 in Physiology of the Bacterial Cell a Molecular Approach, Sinnauer Associates, Sunderland, Massachusetts.
Green et al., "Systematic Screening of Yeast Artificial–Chromosome Libraries by Use of the Polymerase Chain Reaction", (1990) *Proc. Natl. Acad. Sci.* USA 87: 1213–1217.
MacMurray et al., "An Automated Method for DNA Preparation from Thousands of YAC Clones", (1991) *Nucleic Acids Research* 19: 385–390.
Uber et al., "Application of Robotics and Image Processing to Automated Colony Picking and Arraying", (1991) *Bio Techniques* 11: 642–646.
Murray et al., "Rapid, Simple Identification of Individual Osteoblastic Cells and Their Specific Products by Cell Blotting Assay", Journal of Bone and Mineral Research, vol. 4, No. 6, 1989, pp. 831–838.
Viegas–Pequignot et al., Proceedings of the National Academy of Sciences, vol. 86, pp. 582–586.
Pinkel et al., Proceedings of the National Academy of Sciences, vol. 85, pp. 9138–9142.
Lichter et al., Science, vol. 247, 1990, Jan., pp. 64–69.
Manatis et al., Molecular Cloning, A Laboratory Manual, Cold Spring Harbor Laboratory, (1982), pp. 304–305.

*Primary Examiner*—Mindy Fleisher
*Assistant Examiner*—Scott Priebe
*Attorney, Agent, or Firm*—Foley & Lardner

[57] ABSTRACT

Micro-scale methods are applied in producing, maintaining, replicating, screening, manipulating and sub-cloning cell libraries. By means of the micro-scale methods of the invention, micro-libraries of single-cells or micro-colonies arranged in a definite two-dimensional pattern are produced, propagated, replicated, screened, examined and manipulated. It is feasible to sub-clone cells and micro-colonies from the micro-libraries, particularly those identified by screening and examining the micro-libraries, for the purposes of purification and large-scale cultivation. Automated and scaleable methods can be applied to screen practically any collection of cells attached to a surface. These methodologies are useful for making and screening on a micro-scale genomic libraries, cDNA libraries, and libraries of hybridoma cells, inter alia. Similar approaches employ such methods and micro-libraries for toxicological, pharmaceutical, mutagenetic and carcinogenic screening.

18 Claims, No Drawings

MICRO-LIBRARIES FOR SCREENING CELL POPULATIONS

This application is a division of application Ser. No. 07/795,462, filed Nov. 21, 1991, now U.S. Pat. No. 5,326,691.

BACKGROUND OF THE INVENTION

The present invention relates to producing micro-libraries composed of micro-colonies, arrayed on a surface, which can comprise from one to several thousand or more cells. The present invention also relates to methods and means for replicating a micro-library via formation of a replicate, "daughter cell," micro-library in such a way that micro-colonies of the replicate library are in substantially the same pattern as the micro-colonies of the original ("mother cell") micro-library. Additionally, the present invention relates to maintaining, screening, examining and manipulating micro-libraries.

Making and screening banks of cells is an important aspect of many molecular and cellular biological techniques important in laboratory research and in the clinical laboratory setting. For instance, two fundamental endeavors in biotechnology which involve cell banks are gene cloning and production of monoclonal antibodies.

Gone cloning is a tool which is key to nearly all areas of biological research. For instance, it is crucial to producing many pharmaceutical compounds, particularly those of proteinaceous nature. Gone cloning makes possible the elucidation of the genetic basis of many diseases, and it will be a central feature of genetic therapies which may address a variety of dysfunctions caused by alterations in gene expression.

Cloning genes and other DNA segments can be an arduous task, however, and realizing the full potential of gene cloning techniques, a goal of the effort to sequence the entire human genome, is beyond the reach of current technology. For instance, the human genome consists of approximately $3\times10^9$ base pairs per haploid complement. (For an authoritative discussion of genomic and cDNA cloning, including a description of cloning vectors and mathematical considerations in genomic and cDNA cloning, see Sambrook et al., MOLECULAR CLONING, A LABORATORY MANUAL, Second Edition, Vol. 1–3 (Cold Spring Harbor Laboratory, 1989)). An average plasmid cloning vector is able to accommodate perhaps $6\times10^3$ base pairs of heterologous DNA and still be able efficiently to transform recipient cells using conventional techniques.

Accordingly, $5\times10^5$ recombinant plasmids are required to accommodate an entire human genome. Moreover, because cloning involves inherently probablistic procedures, about $3\times10^6$ such plasmids are required for a 99% chance that all of the plasmids together contain every sequence in the human genome. Even this estimate fails to account for loss of sequences that deleteriously affect transformed-cell growth, something that can be a particular problem when regimes of competitive growth are employed in making, propagating or amplifying a library. In any event, the screening of three million plasmid clones is a formidable undertaking that requires a considerable investment of effort, time and money.

Non-plasmid cloning vectors are available which can accommodate larger segments of DNA. Bacteriophage lambda-derived vectors, for instance, can accommodate approximately as much as $2.5\times10^4$ base pairs of heterologous DNA, thus requiring about one million such recombinants for a complete human library at the 99% confidence level. See, for instance, pages 270–271 of Maniatis et al., MOLECULAR CLONING, A LABORATORY MANUAL (Cold Spring Harbor Laboratory, 1982). Hybrid plasmid-phage vectors known as cosmids accommodate even larger inserts, reducing to perhaps one-half million the number of recombinants needed to provide a complete human genome at a 99% confidence level.

Yeast artificial chromosome (YAC) vectors accommodate even larger inserts, potentially as large as $1\times10^6$ base pairs. By the use of YAC vectors, therefore, it is possible at the 99% confidence level to contain a human genome in approximately $5\times10^4$ YAC recombinants. Even such YAC libraries, however, are cumbersome and inefficient to manipulate and time-consuming and expensive to use. For instance, YAC libraries are often propagated in the wells of microtiter plates, for convenience in maintaining the clones of the library in isolation from each other to prevent cross-contamination. For a human YAC library, about 300 to 500 96-well plates are needed to provide the 30,000 to 50,000 wells necessary to maintain separately each clone in the library. See, for instance, MacMurray et al., *Nuc. Acids Res.*, 19: 385 (1991). Screening 300 microtiter plates one time requires considerable effort, repetitive screening, as required by chromosome walking techniques, for example, requires resources beyond the reach of many laboratories.

Thus, even with the most efficient cloning systems currently available each manipulation of a human library represents a considerable undertaking that is expensive of effort, resources, time and money. In consequence, a variety of interesting and important experiments are rendered impractical or can be undertaken only by marshalling large-scale support.

Another problem in isolating particular clones from libraries is the necessity to clonally purify or ("clone-out") positives. Generally, libraries of complex genomes constructed in plasmid and phage-derived libraries are spread or plated at high densities to minimize the number of petri-plates needed to accommodate the library. Colonies and plaques which are identified as being of interest, therefore, cannot readily be separated from nearby colonies or plaques that generally are not of interest. For each positive clone this necessitates multiple rounds of low-density screening and re-isolation to obtain a homogeneously pure isolate. Rescreening positives slows down and adds to the cost of cloning experiments, and can seriously impede or render impractical experiments where libraries are being screened for the presence of several different sequences or where "walking experiments" that require repeated sequential screenings are being carried out.

The necessity of rescreening positives is mitigated or altogether avoided when libraries are initially spread at low densities and then individual clones are picked into individual cultures in separated wells in an array. Ordered libraries are extraordinarily labor-intensive to construct and it is generally impractical to construct ordered libraries for more than a few tens of thousands of clones. (For a discussion of the difficulties even of an automated procedure for making an ordered library see Uber et al., *BioTechniques* 11: 642). Furthermore, such low density libraries are cumbersome to manipulate and expensive to maintain and screen.

For instance, ordered human YAC libraries of have been made by transferring individual clones from an initial library spread at low density into individual microtiter plate wells. Even when semi-automated, however, producing such libraries requires extraordinary effort. Moreover, a human YAC library, even an ordered one, must still contain 30,000 to more than 60,000 clones in 300 to over 600 microtiter dishes, and is very difficult to manipulate and expensive to screen.

Similar considerations apply to a variety of other endeavors where populations of cells are produced, propagated and screened to identify those few cells and/or their progeny that possess a desired characteristic. Such an endeavor is the production of monoclonal antibodies, which usually entails fusing immortalized non-secreting B-cells, such as MOPC cells, with the lymphocytes of spleens from animals inoculated with an antigen of interest. The procedure results in clonally derived hybridoma cell lines, each obtained from the fusion of one MOPC cell and one splenic lymphocyte. The bank of hybridomas produced by each fusion experiment must be screened to identify the few clones that produce an antibody having a desired specificity. Often many fusions must be carried out, and a great number of cell lines must be screened, to obtain a hybridoma cell-line that produces an antibody with desired properties. Since it is necessary to propagate each hybridoma cell-line, or a limited mixture of cell lines, in a different microtiter-dish-well, these experiments also often require numerous micro-titer dishes. Consequently, the experiments are cumbersome and time-consuming to carry out, and incur considerable costs, similar to those required for large-scale cloning projects.

Among other applications where large numbers of different cells must be screened that encounter similar problems are toxicology, mutagenicity and carcinogenicity assays.

In genetic toxicology assays, for instance, indicator cells are exposed to a compound, such as a potential pharmaceutical agent, or to an environmental agent, to assess the agent's toxicity, mutagenicity or carcinogenicity, for instance. A common "indication" method is to score a genetic marker, such as reversion of a mutation that prevents growth on a defined medium. In this type of assay, mutational events are counted by the number of colonies that appear on defined, growth-preventing medium after exposure to a potentially mutagenic agent.

These assays typically proceed by exposing the agent to large numbers of indicator cells. Many separate experiments of this type are carried out to determine dose-response curves with sufficient accuracy to measure mutagenic activity. Each point on a dose-response curve may represent the average of multiple assays, each requiring a separate cell-culture. Thus, establishing a single dose-response curve for an agent on a single type of indicator cell may involve many separate cultures for each type of indicator cell.

In addition to requiring many separate cultures, assays of this type can also be especially time consuming in many cases because the indicator cells may be enfeebled and grow slowly, even after a reversion event, and the assays require macroscopic colonies for scoring. Furthermore, small colonies produced by slow-growing mutants may be overlooked systematically when only large colonies are scored, which results in underestimating mutagenic effects, and misrepresenting test results. Accordingly, assays of this type also are logistically hindered by the need to manipulate large numbers of cell-cultures and to screen large numbers of macroscopic colonies, and they are expensive and time-consuming to perform.

SUMMARY OF THE INVENTION

It therefore is an object of the present invention to provide improved methods for identifying in a population of cells those cells which a express a characteristic of interest.

It is a further object of the present invention to provide screening methods suitable to screening large numbers of cells to detect therein certain cells expressing a characteristic of interest.

It is yet another object of the present invention to provide micro-libraries in which individual cells or small subpopulations of cells replace the macroscopic colonies, plaques and cultures of conventional libraries.

It is still a further object of the present invention to provide methods for making micro-libraries and for containing micro-libraries on one or a few surfaces that allow all the cells or micro-colonies of the library to access a common pool of media in which the library can be propagated. An additional object of the present invention is to provide methods to maintain and propagate micro-libraries.

Yet another object of the invention is to provide methods for replicating micro-libraries.

Yet another object of the invention is to provide methods for screening the micro-libraries to identify within the population of cells of the micro-library those cells or sub-populations of cells that have a detectable characteristic of interest.

An additional object of the present invention is to provide equipment for manually and automatically examining the micro-libraries.

Still another object of the invention is to provide methods for manipulating cells and sub-populations of the micro-libraries, particularly to isolate individual sub-populations from the micro-libraries for clonal propagation.

Another object of the present invention is to provide equipment for manually and automatically manipulating the micro-libraries.

In accomplishing the foregoing objects, there has been provided, according to one aspect of the present invention, a method for generating and analyzing micro-libraries of cellular clones, comprising the steps of (A) providing a population of mother cells that represents a plurality of sub-populations that differ, one from the other, by at least one genetic or phenotypic characteristic; (B) immobilizing the population on a first surface such that the mother cells are retained; then (C) bringing the first surface into proximity of a second surface such that (i) daughter cells replicated from the mother cells come into contact with and are immobilized on the second surface and (ii) the daughter cells immobilized on the second surface are positioned thereon in a spatial relationship with respect to one another which is substantially similar to the spatial relationships with respect to one another of the mother cells immobilized on the first surface; thereafter (D) treating the second surface such that sub-populations of the daughter cells are rendered distinguishable, one from the other; and then (E) examining the second surface to detect the presence of at least one sub-population of daughter cells.

In preferred embodiments the mother cells and daughter cells are bacterial, yeast, insect, plant or mammalian cells. Also preferred are cells that contain genomic clones, cells that contain cDNA clones, cells that express exogenously derived genetic elements, hybridoma cells, cells for mutagenicity testing, cells for carcinogenicity testing, and mixtures of such cells.

In further preferred embodiments the sub-population on the second surface is rendered distinguishable by hybridization to a detectably labelled polynucleotide probe, by a hybridization method comprising the polymerization chain reaction, or by an immunologically reactive reagent. Preferred embodiments include those which utilize radioactive, colorimetric, fluorescent, phosphorescent, luminescent, chemiluminescent, affinity, or enzymatically detectable labels.

Preferred means of replicating the micro-libraries include those wherein the first surface is maintained above the second surface, those wherein a flow of media is maintained perpendicular to the planes of the first and second surfaces when the surfaces are in proximity to immobilize the daughter cells, and those wherein a laminar flow of media is maintained parallel to the planes of the first and second surfaces when the surfaces are in proximity to immobilize the daughter cells.

Further preferred embodiments are those wherein the mother cells are placed randomly on the first surface and the daughter cells are disposed in substantially the same arrangement on the second surface, and those wherein the mother cells are placed on the first surface in a predetermined spatial relationship, and the daughter cells are disposed in substantially the same predetermined arrangement on the second surface.

In accordance with another aspect of the invention there has been provided micro-libraries comprising a plurality of spatially distinct microscopic micro-colonies on a surface wherein substantially every micro-colony contains between 1 and 1,000,000 clonally derived cells. Preferred embodiments of this aspect of the invention, include those wherein the micro-colonies are each 100 to 100,000 bacterial cells, 10 to 10,000 yeast cells and 1 to 1,000 higher eukaryotic cells. Additional preferred embodiments include those wherein the micro-colonies are fixed in a random pattern and those wherein the micro-colonies are fixed in a pattern predetermined by cell-adherent and cell-nonadherent surfaces provided on a support.

Other objects, features, and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

GLOSSARY

ARRANGEMENT, PATTERN, SPATIAL RELATIONSHIP: The cells, micro-colonies, plaques and the like of a micro-library will have a two-dimensional pattern. Any arrangement on a surface is such a pattern. The arrangement or pattern of the micro-library is defined by the relative spatial relationship in two-dimensions of the micro-colonies with respect to one another.

The pattern of a micro-library may be random or non-random. For instance, cells in solution when spread on an untreated glass slide will generally form a random pattern, and the micro-colonies developed from these cells therefore will be arranged in a random pattern. Alternatively, cell and micro-colonies may be disposed in a non-random predetermined pattern, as described hereinbelow.

In general, the pattern of cells and micro-colonies in a micro-library is substantially constant over time. Cells may divide and micro-colonies may grow but their physical location on the surface remains the same or similar. Preferably, the location of any micro-colony is sufficiently constant to locate the micro-colony by its physical co-ordinates on the surface.

In a preferred embodiment the cells of different micro-colonies do not make physical contact or intermingle (overlap). Where cells and, hence, the micro-colonies which develop from them are spread on a surface randomly, overlap of the micro-colonies will be determined by statistical considerations, and it can be minimized by distributing cells initially at lower surface densities, and by minimizing the number of cells in the micro-colonies.

The pattern of daughter-cell micro-colonies in a replicate micro-library will be substantially similar to the pattern of mother cell micro-colonies in the mother cell micro-library. The similarity of mother-cell and daughter-cell micro-colonies will permit correlation between a given daughter cell micro-colony and the originating mother cell micro-colony. By extension, therefore, clonally derived progeny of an original micro-colony can be identified in replicates of a micro-library by their physical location, which will be the same relative to the pattern of the micro-library in all micro-library replicates.

The pattern of the daughter-cell micro-colonies in the daughter-cell micro-library will be statistically representative of the pattern of mother-cell micro-colonies in the mother-cell micro-library. That is, the daughter-cell micro-colonies will be arranged in substantially the same pattern as the micro-colonies of the mother-cell library. A daughter-cell micro-colony may drift away from the exact position occupied by an originating mother-cell micro-colony. For instance, daughter cells may be somewhat displaced during micro-library replication as they move from the surface of the mother-cell library to the surface of the daughter-cell library. Diffusional effects, for instance, will cause some random displacement of this type, which, therefore, will cause minor random variation of the locations of the daughter-cell micro-colonies relative to the corresponding mother-cell micro-colonies. This type of variation will not alter the overall pattern of the micro-library, and additional overlap among the daughter-cell micro-colonies may be minimized by the spacing the mother-cell micro-colonies further apart, and minimizing their size.

In any case, the pattern of the replicate micro-libraries will remain similar enough that corresponding micro-colonies, which are clonally derived from a single mother-cell micro-colony, can be identified in each replicate of a micro-library by relative physical location in the micro-library pattern. Identification of corresponding micro-colonies thus can be achieved by superimposing images of micro-libraries, so as to align the substantially similar patterns and identify corresponding micro-colonies therein. In certain preferred embodiments of the invention, wherein replicates are formed on precisely shaped and registered surfaces, corresponding micro-colonies may be identified by virtue solely of physical location on the surface, without necessity to superpose images.

Furthermore, the patterns of micro-libraries will remain substantially the same throughout the processes or maintaining, propagating, replicating, storing, screening and examining the micro-libraries.

MICRO-COLONY: "Micro-colonies" in the present description are sub-populations of clonally derived cells that form elements of the population of a micro-library (see next definition). Generally, micro-colonies will contain about one cell to about several hundred-thousand cells, depending on the type of cell of which it is composed. In any event, a micro-colony will not be large enough to be visible to the unaided eye.

Although much of the discussion herein refers to micro-colonies of cells, it will be readily appreciated that additional cell-mediated phenomena are useful in the invention in the same way as cellular micro-colonies. Thus, phage vectors can be used in accordance with the invention to provide micro-libraries in which the elements are micro-plaques rather than micro-colonies and foci of eukaryotic viral infection likewise can be elements in a micro-library.

MICRO-LIBRARY is a population of individual cells or small sub-populations of individual cells (micro-colonies), the members of which differ from each other in their genotype and/or their phenotype. When the micro-library consists of small sub-populations, the sub-populations generally will consist of about one cell to about several hundred thousand cells, although larger numbers of cells may be used. The number of cells in the sub-populations of the micro-library, and the size of the micro-colonies will depend on the type of cell employed and the purpose of the library.

Generally, the population of the micro-library is arranged in a definite two-dimensional pattern which is substantially replicated as the micro-library is propagated and replicated by means of the invention described herein.

Illustrative examples of the types of micro-libraries that can be made in accordance with invention include genomic libraries, cDNA libraries, expression libraries, libraries of cells transformed with randomly mutagenized DNAs, hybridoma banks, and banks of cells useful for testing for toxicological, pharmaceutical, mutagenic or carcinogenic effects.

Each element in a micro-library is one or a limited number of mother cells or daughter cells, unlike a conventional library, which generally has as each element a plaque or a colony consisting of, for instance, in bacteria, approximately $10^6$ cells (or viruses). For yeast or mammalian cells the number is lower, but, in any case, each element in a conventional library is macroscopic, whereas each element in a micro-library is microscopic. Furthermore, conventional libraries at high density cannot be replicated in a definite two-dimensional pattern consisting of well separated elements, whereas the micro-libraries of the invention at similar or higher densities provide well defined elements (e.g., micro-colonies) in a definite two-dimensional array.

Thus, whereas the primary two-dimensional pattern of a micro-library can be replicated directly, so that it is an ordered library, the production of ordered conventional libraries requires picking individual plaques or colonies from a primary plate into an ordered array on a second plate, such as a microtiter dish, a time-consuming process that is difficult even for human/YAC yeast libraries and is impractical for larger libraries. MOTHER-CELL, MOTHER-CELL LIBRARY: The term "mother-cell" is used herein to denote cells which give rise to daughter cells. Mother-cells also may be called primary cells. Thus, initial transformants in a library construction, e.g. the cells that initially take up DNA in a transvection, transfection, transformation, or infection, etc., may be called mother-cells. However, the term is also used to denote any cells that give rise to progeny cells. Any population of mother-cells may constitute a mother-cell library as the term mother-cell library is used herein. Moreover, a mother-cell library may be replicated to form a daughter-cell library, and the daughter-cell library may then serve as a mother-cell library when it is replicated to form a daughter-cell library composed of its own progeny.

DETAILED DESCRIPTION OF THE INVENTION

The present invention overcomes many of the disadvantages of conventional methodology by allowing one to make, propagate, screen and manipulate banks of cells on a microscale, i.e., on the scale of a few hundred thousand cells or fewer. In particular, the present invention provides extremely high density libraries of cells, denoted "micro-libraries" herein, immobilized on a surface in a fixed arrangement which, by means of the invention is replicable thereafter. Further, the present invention allows for maintaining the cells in a micro-library in a viable state. Also provided are methods to replicate the micro-libraries. In accordance with the present invention, any first micro-library immobilized on a first surface is replicated by immobilizing daughter cells of the cells in the micro-library on a second surface in the same arrangement as the mother cells on the first surface.

It is also practicable with the present invention to screen a mother cell micro-library or the daughter cell replicates by a variety of means, including, inter alia, methods that comprise hybridization to a polynucleotide probe, reaction with an antibody, or direct detection of enzymological activity.

The present invention entails means for examining the outcome of screening procedures to detect a clone of interest. Illustrative of such means are the use of charge-coupled devices to scan micro-libraries and to provide an image signal suitable to computerized image enhancement either for automated analysis or analysis by a human operator. Micro-libraries can be aligned with images that result from screening procedures to identify in the micro-library those micro-colonies that generate a signal corresponding to a characteristic of interest. Alignment can be carried out using high-resolution micrometer movements, which allow rapid positional identification of clonally related micro-colonies in any replicate of a micro-library.

Another aspect of the present invention involves manipulating or isolating micro-colonies of interest, e.g., for sub-cloning cells which generate a positive signal in a screening experiment.

In accordance with the foregoing, the present invention relates to micro-scale methods for producing and manipulating (including sub-cloning) cell libraries. More specifically, mother cells are immobilized on a surface, forming, essentially, a library of single cells or micro-colonies. Daughter cells of the mother cells are immobilized on a second surface to form a replicate of the mother-cell library, in which the daughter cells are spatially disposed in substantially the same pattern as the mother cells in the mother-cell-library. The replicates themselves can be used further to propagate the library in the same manner, thereby allowing for the rapid propagation and replication of such a library while maintaining the original spatial arrangement of the mother cells.

Thus, the present invention affords methods to make, replicate, maintain, screen, examine and manipulate banks of cells in the form of micro-libraries which contain high densities of micro-colonies. The invention thereby provides methods for screening very large numbers of cells, with a plurality of probes, quickly and inexpensively, and to manipulate and/or isolate and/or propagate particular cells of interest from the micro-library.

Replicates of the mother-cell-library, pursuant to the present invention, can be screened using detectable labels to identify sub-populations of daughter cells that are distinguished by the presence or absence of a phenotypic and/or genetic marker. Micro-clones of the daughter cells can be formed in the replicates.

The present invention also enables the microscopic examination of replicates in order to identify sub-populations of cells distinguished by the detectable label. The microscopic examination can be carried out manually by an observer using conventional microscopy equipment. Alternatively, it can be performed in semi-automated or fully automated fashion, using video imaging equipment and computerized image-generating, -enhancing and -analysis techniques.

The inventive methodology described herein is also suitable for the isolation, sub-cloning and propagation, in small or large culture, of the cells of sub-populations identified by screening the replicates.

Pursuant to the present invention, mother cells attach to a first surface and daughter cells to a second surface. Surfaces suitable for use in the invention include any surface to which a cell-type of interest will attach with sufficient reproducibility and be retained with sufficient tenacity for making, maintaining and replicating mother or daughter cell arrays.

Such surfaces include but are not limited to surfaces of polystyrene and treated polystyrene surfaces commonly used in cell culture, plastic and glass surfaces, which may be untreated or treated to aid cell attachment, including those treated with generic preparations e.g., poly-L-lysine, collagen, fibronectin, laminin and the like, or with proprietary preparations like "CELL-TAK" (available from Collaborative Research) an adhesive protein from a marine mussel, and "MATRIGEL," which aid and promote cell adherence. In addition, cell layers such as feeder layers and the like can be employed to promote cell adherence in accordance with the present invention. Transparent materials and materials suitable for cell imaging using reflected light are preferred to facilitate examination of the cells in a micro-library.

In a preferred embodiment, microporous membranes are employed as surfaces for making, propagating, replicating, and screening micro-libraries. Such microporous surfaces are especially advantageous inasmuch as they promote higher densities of cell growth, provides better access to media, and/or allow cells to form three-dimensional micro-colonies which penetrate shallowly into the pores of such membranes, facilitating the replication of the micro-colonies by direct contact between surfaces. A variety of commercial microporous membranes, much used in other areas of cell culture, are suitable for use in the present invention. An exemplary membrane of this type is the MILLICELL insert membrane sold by Millipore, which is advantageously transparent and can be used to grow virtually any type of cell. Thus, over sixty different types of pure and mixed cell cultures, including primary culture and immortalized cell lines, have been cultured on MILLICELL inserts.

In fact, a variety of surfaces suitable to the reproducible immobilization of naturally adherent and non-adherent cell-types can be used in the invention. Such surfaces provide for the immobilization of mother cell micro-libraries or daughter cell micro-libraries comprising cells of any type, including bacterial, yeast, insect, plant and mammalian cells In addition to surfaces that adhere cells in general, surfaces that retain only specific types of cells can be used in practicing the present invention. For instance, nonadherent surfaces coated with cell surface specific antibodies can be used to immobilize selectively only cells that present a cognate antigen, thereby providing for the immobilization from a mixed population only those cells expressing a predetermined characteristic (i.e., the cognate antigen in this example).

In addition to the interaction between antibody and antigen, a variety of affinity interactions can be exploited in accordance with the present invention selectively to immobilize cells on a surface. For example, sugar-lectin binding, ligand-receptor binding and substrate (or substrate analog)-enzyme binding can all be employed to immobilize cells selectively.

By the same token, specifically retentive surfaces can be used in making micro-libraries to select transformants from the background of non-transformed cells, or in making hybridoma banks to select fused cells from non-fused precursors, or in further selecting antigen binding hybridomas from those which produce antibodies which do not bind the antigen.

Complex surfaces also can be formulated, for instance, to provide conditions suitable to growth of fastidious cells. One application of this type utilizes the CD40 system, which provides long-term in vitro culture of human B cells, thereby to produce libraries of cells that produce human antibodies. (Banchereau et al., Nature 353: 678 (1991), provides a detailed overview of the CD40 lymphocyte culture system in detail). Thus, in a preferred embodiment, a surface on which a human B-cell micro-library (which may also be called a cell bank) will be formed is coated with a feeder layer of transfected mouse L tk fibroblast cells that express on their surface an Fc-receptor (most preferably Fc$\gamma$RIICDw32 cells). The feeder layer cells are "coated" with monoclonal antibodies against the CD40 antigen, which bind to the Fc receptor. A sample containing B-cells is incubated with the surface so that the B-cells are retained by binding to the anti-CD40 monoclonals. The B-cell-containing samples can be obtained from human tonsils, spleen and blood, among other sources, or from similar tissues of other animals. The B-cells which are retained are stimulated to proliferate both by the fibroblasts, by the anti-CD40 monoclonal and by the use of appropriate media and media additives, such as cytokines, particularly IL-4.

Thus stimulated, each B-cell can form a micro-colony which together constitute a micro-library of human antibody-producing B-cells which can then be screened for antibodies specific for a particular antigen, among other uses.

In yet another useful application the methods of the invention can be used to fish-out, examine and/or clonally propagate fetal cells from maternal fluids. For instance, a first surface may be coated with an antibody to a fetal-specific antigen, and then brought into contact with a sample of blood obtained from a pregnant female, for instance. After sufficient time for fetal cells to bind to the fetal-specific antibodies on the surface, unbound sample is washed away, and the surface is incubated under conditions suitable to examination and/or propagation of the fetal cells. It will be understood that such fetal-cell micro-libraries may be replicated, examined, screened, manipulated and the like the same as any other micro-library.

It will be appreciated that selectively retentive surfaces as described hereinabove can be used for variety of other purposes, such as selectively immobilizing caner cells from a clinical sample.

In a preferred embodiment, micro-libraries of indicator cells also can be immobilized on portions of the first surface, prior to exposure of the surface to the sample. These cells will be screened and examined along with cells from the sample, providing internal controls to standardize screening procedures. The control cells most often will be immobilized as replicate micro-libraries, thus facilitating the preparation of many standardized surfaces that provide indicator cell controls.

Surfaces for making micro-libraries may also comprise a mixture of cell-adherent and cell-nonadherent surfaces.

Since these surfaces can be distributed in any pattern, the use of cell-adherent and cell-nonadherent surfaces provides means to attach cells to a surface in a predetermined two-dimensional patterns, e.g., to form ordered micro-libraries.

A pattern in the attachment of cells can be obtained by coating a support with one or both of a cell-adherent material and a cell-nonadherent material so that a pattern of cell-adherent surfaces and cell-nonadherent surfaces is formed. With such a support, cells would attach to the cell-adherent surfaces but not to the cell-nonadherent surfaces, thereby distributing the cells into the pattern of the cell-adherent surfaces.

As indicated above, any support is suitable that provides a surface for growing cells. The support can be treated to provide surfaces with improved qualities for growing cells. The support can also be treated to provide a multiplicity of cell-adherent and cell-nonadherent surface. The ultimate cell-attachment surface may be formed on the support via a multiplicity of intermediate surfaces.

Adherent surfaces useful for forming such patterns include, among others, those discussed above for forming and propagating micro-libraries. Useful nonadherent surfaces include any cell-nonadherent substance which is compatible with generating, maintaining, propagating, replicating, screening, examining and manipulating a micro-library. Suitable nonadherent surface do not deleteriously affect cells on neighboring adherent surfaces. Illustrative of preferred nonadherent surface materials is polyHEMA.

The pattern of adherent and nonadherent surfaces can be formed by any suitable means. For instance, such a pattern could be produced by photolithographic techniques similar to those which are conventional to the semiconductor arts. Thus, a mask could be produced, first in macroscopic form and then in photoreduced format, in the desired pattern of cell-adherent or cell-nonadherent surface. The mask then would be used to control the distribution of adherent or nonadherent materials on the micro-library support.

Such a mask could be used in conjunction with a variety of means for distributing the adherent or nonadherent surfaces. For instance, the materials of the surfaces could be diffused in a vacuum through the mask and onto the support. By another approach, coating materials could be sprayed through the mask. Alternatively, materials could be coated over a mask maintained tightly in contact with a support. In any case, the mask would define the pattern of surface-coating.

In one embodiment, therefore, a uniformly cell-nonadherent surface of a suitable micro-library support would be exposed, through a mask, to a cell-adherent material. The adherent material would cover the nonadherent surface in the pattern dictated by the openings of the mask, providing a predetermined pattern of cell-adherent and cell-nonadherent surfaces which in turn would determine the pattern of cells and micro-colonies of a micro-library immobilized on the surface.

Other means could be employed to generate such patterns for immobilizing cells in a predetermined array. For instance, adherent or nonadherent surfaces could be painted directly onto a support in a predetermined pattern. In this context, the cell adherent or nonadherent materials could be applied by a computer-controlled micro-applicator. In yet another embodiment of the invention, cell adherent and nonadherent materials could be squirted onto a surface in the desired pattern in a manner similar to the deposition of print by an ink-jet printer.

It will be understood, in view of the foregoing description, that the basic techniques for forming patterns can be elaborated to accommodate selective immobilization of complex mixtures of cells. For instance, a variety of antibodies or other selective cell-binding agents can be immobilized on a surface in a predetermined pattern to generate an ordered micro-library comprising a variety of cell-types always in the same predetermined pattern.

Cells suitable for use in accordance with the present invention include any cell-type or mixture of cell-types that usefully may be employed to make banks of cells for screening purposes or to propagate a genetic element and/or a phenotypic marker. Prokaryotic (bacterial) cells such as $E.$ $coli$ cells and eukaryotic cells, including but not limited to yeast, insect, mammalian (mouse, rat, hamster and human, inter alia) and plant cells, are suitably employed in the present invention. Bacterial, especially $E.$ $coli,$ yeast and mammalian cells are particularly preferred cells of the invention.

Micro-libraries may be composed of a single cell-type or of several different cells types. When different cell-types are cultured on the same surface they generally will be compatible with a single growth medium. The density of cells in micro-colonies and of micro-colonies in a micro-library can be adjusted to conform with the requirements of a particular application. Those skilled in the field will appreciate, for instance, that one way to obtain better separation between colonies is to maintain fewer micro-colonies per slide. In addition, the parameters of cell and micro-colony density will be determined to some extent by the size and growth habits of the cells themselves.

Thus, $E.$ $coli$ bacteria are elongated, approximating a circle 1 μm in diameter, and could grow on a surface at densities of about $1 \times 10^6/mm^2$. Accordingly, some $1 \times 10^9$ cells can be cultured in an area of 1,000 $mm^2$, approximately the working area of a standard slide (2.5 cm by 5.0 cm). This density would provide about $1 \times 10^4$ to about $1 \times 10^6$ $E.$ $coli$ micro-colonies containing about $1 \times 10^3$ to about $1 \times 10^5$ cells in the working area of a standard slide, and as many as $1 \times 10^9$ single-cell micro-colonies in this area.

Yeast are approximately 5 μm in diameter and can grow on a surface at densities of approximately $4 \times 10^4/mm^2$. Therefore, about $4 \times 10^7$ yeast cells can be cultured in 1,000 $mm^2$, providing from about $1 \times 10^5$ or less to about $4 \times 10^6$ micro-colonies or more, each with about 10 to about 400 cells, and as many as about $4 \times 10^7$ single-cell micro-colonies.

Lymphocytes are relatively small eukaryotic cells, typically mammalian, that have a diameter of approximately 30 μm. Therefore, lymphocytes can be attached to a surface at a density of about 1,000 cells/$mm^2$, providing $1 \times 10^6$ lymphocytes in 1,000 $mm^2$. Consequently, between about $1 \times 10^3$ or less and about $1 \times 10^5$ or more micro-colonies containing between 10 and 1,000 cells each can be accommodated in approximately the working area of a single slide. In preferred embodiments of the invention, micro-colonies of lymphocytes, or other similarly sized cells, contain 20 to 400 cells.

Fibroblasts are larger eukaryotic cells that occupy a surface area of about 5,000 $\mu m^2$. These cells can be cultured on a surface at a density of about 200/$mm^2$, corresponding to roughly $2 \times 10^5$ in 1,000 $mm^2$. Thus, between 2,000 or less and 20,000 or more micro-colonies of between 10 and 100 cells, up to $2 \times 10^5$ or more single-cell micro-colonies, may be maintained in an area approximating the working area of a single standard microscope slide. In preferred embodiments of the invention, micro-colonies of fibroblasts, or other similarly sized cells, contain 10 to 50 cells.

Micro-libraries having very high densities of micro-colonies, comprised of practically any cell-type, can be obtained pursuant to the present invention.

The utility of the inventive technique can be appreciated from a consideration of its application, for example, to a human-yeast/YAC library which provides a complete human genome at the 99% confidence level. As indicated above, a human genomic library can be accommodated in a yeast/YAC library of roughly 60,000 individual clones, and as many as $4 \times 10^7$ yeast cells can be accommodated on a surface of 1,000 mm$^2$. Accordingly, the entire library might be propagated is the working area of a single slide in the form of roughly 60,000 micro-colonies of approximately 650 cells each. Alternatively, to provide more distinctly separated micro-colonies, the library can be propagated as 60,000 micro-colonies of 200 cells each, with the remaining 66% of the area remaining free of cells.

From the foregoing it is apparent that micro-libraries can be configured to a desired purpose, limited only by the characteristics of the cells from which the library is constructed. Maintaining and propagating micro-libraries can be accomplished readily by using the standard cell-culture techniques appropriate to the cell-type(s) of the micro-library. Thus, micro-libraries on slide(s) can be maintained by immersing the slide(s) in appropriate medium, which is then incubated under conditions suitable to growth or maintenance of the cell-types in that micro-library. Because the number of cells in the micro-library is low, media requirements are minimal. Also, because the cells and micro-colonies in the micro-library are immobilized, the entire population of the micro-library may be co-immersed in the same pool of media, without problems due to cell loss and/or cross-contamination.

More elaborate systems for maintaining micro-libraries also can be employed in accordance with the present invention. Such systems include fully automated systems for incubating large numbers of micro-libraries simultaneously.

Further, the invention provides methods to replicate micro-libraries. Mother cells immobilized on a first surface in accordance with the invention are provided with conditions and media to grow and divide, without detaching from the surface. By contrast, the progeny of the immobilized mother-cells do not immediately attach to the first surface and therefore can be immobilized readily on a second surface brought into appropriate proximity of the first surface to contact the budding progeny cells. In some instances, contact between the second surface and the budding progeny cells may take place somewhat before cell division is complete and the mother and daughter cells have separated completely. In other situations the progeny cells may separate from the mother-cells and pass through a distance between the first and second surfaces before contacting the second surface and immobilizing thereon.

Movement from the first to the second surface may be facilitated by placing the first surface above the second surface so that, in essence, progeny cells drop from the first onto the second surface, under the influence of gravity.

More involved systems can be employed to facilitate the transfer of progeny cells to the second surface with little or no lateral diffusion or other loss of positional information as a result of cell-division, transit across the gap between the two surfaces, or immobilization on the second surface. For instance, an electric field may be applied orthogonally to the planes of the surfaces to cause progeny cells to travel to the second surface quickly and by a most direct route.

Alternatively, laminar flow along the direction perpendicular to the planes of the surfaces may be generated to carry the cells to the second surface directly along a surface orthogonal path. Simple wicking action through a microporous membrane surface is one method to provide this type of flow.

The first and second surfaces are brought into appropriate proximity and maintained therein for a time that depends on the cell cycle of the cells of the micro-library under the particular conditions of growth employed for maintenance, propagation and replication of the micro-library. Thus, the exact time and conditions suitable to replicating a particular micro-library can be determined empirically.

Generally, such a determination can be accomplished by bringing the first and second surfaces into proximity and following the process of cell-division under a microscope. Establishing the timing of the cell-cycle of cells in a micro-library should be done under the conditions ordinarily to be employed for growing and replicating the micro-library. In addition, propagation and replication of micro-libraries ordinarily will be monitored by microscopic, video and/or charge-coupled device (CCD) image-generating and magnifying techniques.

Bringing the second surface into and maintaining proximity of the first surface can be accomplished by any suitable means. Pursuant to one embodiment of the present invention, spacers machined to provide the correct spacing are interposed between the first and second surfaces. The spacers are fixably attached to the first or second surface or, to both surfaces. The spacers can be of any material compatible with cell viability and propagation which can be formed with the required precision. For some applications, spacers of an inert material such as teflon are preferred.

In another embodiment, both surfaces are fixed in a mechanical device such that the distance between them can be adjusted by means of a micrometer movement. In this context stepper motors could be used to adjust the interfacial distance between the surfaces.

A device of this sort would be attached to a microscope stage which provides micrometer-controlled movement in two or three orthogonal directions of the surface planes, and also could provide micrometer-controlled rotational movement about an axis normal to the surface planes. Such an arrangement would allow for ready microscopical examination of all the cells in both a mother-cell micro-library and a daughter-cell replicate, e.g., during the process of replicating the micro-library. The stage movement also would be useful for micromanipulation of the cells on the surfaces, as described in greater detail below.

In another embodiment, the movement in all directions in a device of the type described in the preceding paragraph is controlled by stepper motors, which may be manually or computer driven. Furthermore, the image of the cells is digitized and presented for observation on the display screen of a cathode ray tube. The digitized signal would be processed to clarify cell features or for other purposes. Additionally, the digitized image could be used as part of an automated system for propagating, replicating, screening and/or examining micro-libraries.

While the two surfaces are maintained in close proximity for micro-library replication, the proper growth conditions must be maintained for both mother and progeny-cells. In many cases, media, including oxygen tension, in the interfacial gap is sufficient to maintain cell viability and growth throughout the period of contact required to replicate the micro-library. In other instances it may be desirable to provide fresh media to the cells during replication. Accordingly, fresh media may be provided by any suitable means. For instance, the interfacial distance may be adjusted periodically during the replication period to draw in fresh media at appropriate intervals.

Alternatively, a lateral flow of media may be maintained through the interfacial gap. Lateral flow will be kept sufficiently slow and steady, so that displacement of daughter cells along the direction of flow, as they travel between surfaces, will be negligible and/or the same for all daughter cells, thus insuring that the two-dimensional pattern of mother and daughter-cell micro-libraries is the same.

By yet another approach, a flow of media can be maintained across the interfacial gap perpendicular to the surfaces, using microporous surfaces, for instance. This type of flow will also facilitate the transit of daughter-cells from the first to the second surface, as described above.

Micro-libraries can be screened by conventional library-screening, cytogenetic and immunohistochemical methods. Indeed, the entire panoply of techniques which have been used to examine or screen individual cells, cells in colonies, and cells in tissues can be adapted readily to use in practicing the present invention.

Genomic and cDNA micro, libraries, for instance, can be screened by hybridization using polynucleotide probes. The polynucleotide hybridization probes can be prepared by conventional methods. Thus, synthetic oligonucleotide, restriction fragment, plasmid and phage DNA probes can be employed, inter alia, as can RNA probes such as those produced using plasmid-borne T3, T7 and SP6 promoters and RNA polymerases. Many such methods are well known to the art and are described, for example, in Maniatis and Sambrook, supra.

Furthermore, nucleic acid targets in a micro-library may be detected, quantified and localized via the polymerase chain reaction (PCR), as well as by any other method of nucleic acid amplification. In a PCR detection method, for instance, the cells in micro-libraries and micro-library replicates would be fixed to afford access to the polynucleotide probes, generally synthetic oligonucleotides. The fixed preparations would then be treated to reduce non-specific binding of detectable label. After that, the fixed and blocked preparations would be hybridized to the probe oligonucleotides under conditions that provide a desired degree of specificity of duplex formation between the probes and potential target molecules in the fixed cells. At same time, or immediately after hybridization, the fixed sample would be exposed to a solution containing DNA polymerase, preferably a thermostable DNA polymerase, and appropriate polymerization substrates and buffer reagents, and subjected to a program of repeated DNA polymerization and melting reactions, using, for instance, a thermocycling apparatus. All steps in the procedure will be performed in situ. The detectable label generally will be present in one of the DNA polymerase substrates, e.g., a biotinylated nucleoside triphosphate, or will have been incorporated into a probe molecule, such as a biotinylated oligonucleotide, as described in more detail below. After thermocycling, excess labelled substrate is washed away, for instance, simply by immersing a slide containing a micro-library in any suitable washing solution. The detectably labelled, amplified product is then determined for visualization of positive micro-colonies. For instance, biotinylated probe may be detected by incubation with an avidin-alkaline phosphatase conjugate, removing unbound conjugate, and visualizing the amplified biotinylated polynucleotide product using a colorimetric reaction catalyzed by alkaline phosphatase. Many such methods are known in the art, and their applicability to the invention herein described will be apparent to those of ordinary skill.

The probes can be labelled using any detectable label, including but not limited to radionuclide, colorimetric, fluorescent, phosphorescent, luminescent, chemiluminescent, affinity- and enzymatically-detectable labels. Among the affinity-detectable labels are sugars that bind lectins; ligands like biotin which bind with specificity to receptors (avidin or streptavidin in the case of biotin); and haptens, such as digoxigenin, which bind with specificity to cognate antibodies or derivatives thereof.

In the case of affinity labels, detection will often involve an enzyme-mediated reaction with a colored or luminescent product. In one system commonly used for this purpose, biotinylated probe is incubated with a micro-library under conditions that promote hybridization of the probe to its complementary sequence in the genetic complements of the cells of the micro-library. Excess probe which does not hybridize is washed away from the micro-library, and the library is then incubated with, for instance, a alkaline-phosphatase-avidin complex, which binds specifically to biotin in the hybridized probe. Excess conjugate is then washed away, and the micro-library is incubated in a solution containing a chromogenic or chemiluminogenic substrate of alkaline phosphatase. The alkaline phosphatase of the conjugate then generates a colored or chemiluminescent signal which is localized to the particular cells or sub-populations in the micro-library that have bound the hybridization probe.

For many applications it will be preferable to screen micro-libraries directly. But it is also possible, when desirable, to immobilize the material to be detected on a surface apart from the micro-library, in much the same fashion as replicate libraries, retaining the two-dimensional pattern of the micro-library, and to screen the immobilized material for a polynucleotide sequence, protein, antigen, etc., using any of the known techniques for performing such experiments.

While in some case it may be desirable to lyse the cells in the micro-library, thereby to release material for immobilization on the same or on a separate surface, in other cases cell viability can be maintained and only secreted products immobilized on a separate surface. This technique will prove especially useful for screening secreting hybridoma banks and expression systems designed to secrete a heterologous protein. For instance, hybridomas that produce antibodies specific for an antigen, may be identified, in a hybridoma micro-library, by bringing into contact with the micro-library a second surface coated with the antigen. After a suitable wash regimen, antibodies specifically bound to the antigen on the second surface may detected by conventional means, such as secondary antibody EIAs. The position of these antibodies identifies in the micro-colonies in the micro-library those hybridomas that produce antigen binding antibodies.

A wide variety of detection techniques can be used in the present invention. For instance, a colored, fluorescent or luminescent signal can be detected by photomicrographic techniques. Cells distinguished by the production of a colored product thus can be detected by ocular microscopic examination. Alternatively, the micro-libraries can be photographed through a microscope and the photomicrograph can be examined to identify cells or sub-populations which produce a colored product. Additionally, the micro-libraries can be examined by means of a videomicroscope, optionally with computerized image enhancement and/or computerized image analysis. Along similar lines, the micro-libraries can be examined using CCDs to transduce into electronic signals the visual image of the cells of the micro-library.

In a preferred embodiment, chemiluminescent or radioactive signals would be detected autoradiographically. As part of the screening process, for example, the micro-libraries would be coated in photographically sensitive emulsion which records the light or other radiation emitted by bound probe molecules. The emulsion would be exposed to the micro-library long enough to achieve an appropriate signal-to-noise ratio. Upon development, grains would appear in the emulsion at high densities over cells which have specifically bound the labelled probe.

A micro-library often will be stained with a general cellular stain in conjunction with the screening procedure, in order to improve visualization of cell morphology and the overall pattern of the cells in the micro-library. Similarly, staining techniques can be used to aid visualization of other subcellular features of the cells in a micro-library, such as chromosomes, for instance, in accordance with the invention. Staining of this type makes it easier to locate positive and negative cells in the two-dimensional pattern of the micro-library, and facilitates identification of corresponding cells in other replicates of the same library.

Diverse techniques for staining and in situ autoradiography of cells, suitable for use in conjunction with the present invention, are well known in the art.

The micro-libraries of the invention can be read during screening with any instrument capable of transducing the information contained in the micro-library into a from accessible to human interpretation. Devices for reading micro-libraries include conventional light microscopes such as those designed specifically for viewing cells in culture and those designed for viewing cells on microscopy slides, inter alia.

Additionally, micro-libraries can be read more directly by the using, for instance, a CCD. In this regard a signal, typically produced in the course of screening the micro-library, would be detected directly by a microelectronic sensor capable of resolving the individual cells or micro-clones of the invention. Charge-coupled devices provide high densities of sensing elements which are preferred in this type of embodiment of the invention. For instance, currently available CCDs provide nearly 1000×1000 elements per square centimeter (approximately 2000×2000 per square inch) allowing resolution of features on the order of a few micrometers on each side. This allows CCD mediated detection of well spaced single cells or a small number of cells, detectably labelled with an appropriate probe.

One or more individuals cells may be isolated from particular micro-colonies within a micro-library using commercially available micro-manipulators that may be adapted to this purpose, or commercially available stations designed specifically for cell manipulation. "NARISHIGE, INC." is one of many suppliers of equipment suitable to this purpose.

Generally, manipulators for use in the connection with the invention will be capable of controlled sub-micron movement, but any micro-manipulator which can be used to isolate one or more individual cells should be suitable for use in accordance with the present invention.

The micro-manipulation of the cells may be carried out manually using a "joystick" or other control device to maneuver a tool under a microscope to pick up cells from a micro-colony. Generally the cells and micro-colony of interest will be clonally related to a micro-colony yielding a positive signal in screening a mother-cell or replicate of the same micro-library.

A variety of micro-tools can be fashioned to pick up a cell or micro-colony of interest. Such tools can be fabricated from glass by means of a microforge and/or a micropipet puller, according to techniques well known in the art. Furthermore, commercial devices for drawing up and/or dispensing micro-volumes of liquid are readily adaptable to this purpose.

Micrometer movements such as those attached to a microscope stage, which are designed to control "X" and "Y" movement in the plane perpendicular to the path of the light through the microscope, and, movement in the "Z" direction, along the light-path, may be used in accordance with the invention to control the position of slides containing micro-libraries for imaging and micro-manipulation.

Micrometer movements may be manually driven, or they may be driven by stepper motors which may be manually or automatically controlled.

Thus, micro-libraries can be made and replicated and the replicates can be screened to detect a sub-population of interest among the cells or micro-colonies of a micro-library. The results of screening can be examined by microscopy or using a CCD, among other approaches. Particular micro-colonies which score positive can be identified in each replicate micro-library, by virtue of their position in the fixed pattern of the mother and daughter cell micro-libraries.

Cells from each micro-colony of interest can be picked up from the library surface using micro-manipulator equipment as described above. Similarly, after the cells are obtained from the micro-library they can be transferred from the micro-tool to a fresh surface or to liquid media for clonal propagation.

The entire process can be carried out manually, using hand-driven equipment and a light microscope of suitable magnifying power which can visualize the signal generated by the detectable label. It should be most convenient in general to produce during micro-manipulation a real-time video image of the micro-library replicate which is to supply the cells for clonal propagation, and to superpose this image on an image of the screened replicate of the micro-library which shows the micro-colonies that produced a positive signal. The ability to superpose the results of screening on a viable cell micro-library, and/or an image thereof, facilitates identification of micro-colonies corresponding to the screening signal. Videomicroscopy equipment which is commercially available can be adapted readily to this purpose without substantial modification.

Moreover, micrometer movements can be controlled by computer using computer-driven stepper motors. An arrangement of this type can be used to automate the process of aligning a micro-library with an image, such as an image of screening results. In fact, precision drives are commercially available that allow automatic positioning a slide in a carrier to within a fraction of a micron, reproducibly from one slide to the next. With equipment of this type, a stage can be automatically programmed to position a positively reacting micro-colony under the micro-manipulator, in the field of the microscope or other imaging system, by providing co-ordinates generated solely from examination of the screened micro-library. At a higher level of mechanization, it will be possible completely to automate the process of recovering cells from micro-colonies by automating the micromanipulation step, as well as the step of image superposition.

In one embodiment of the present invention, micro-libraries are cultured initially on a light-sensitive surface which then can be cut with a laser to segregate a micro-colony of interest. After such a laser-cutting step, the entire surface except the areas identified by ablation would be removed from the slide, i.e., from the solid support of the micro-library. Instruments suitable to this purpose are commercially available. For instance "MERIDIAN INSTRUMENTS, INC." markets a product for this type of laser ablation called the "COOKIE-CUTTER" technique, which can be used their ACAS 570 interactive laser cytometer, which itself can be adapted to the examination and manipulation of micro-libraries as described here.

The present invention is further described by reference to the following, illustrative examples.

EXAMPLE 1. IMMOBILIZATION OF MICRO-COLONIES ON SURFACES UNDER SELECTIVE CONDITIONS

Sterilization of slides

As a routine matter in these experiments, slides were sterilized by immersion in 70–95% ethanol for 10 minutes in a sterile plastic culture plate ("LABWARE" bacterial growth plates), then were drained briefly to remove as much ethanol as possible, and were allowed to dry for approximately one hour in a fresh, sterile culture plate, in a laminar flow sterile hood.

"Spiked" Yeast Primary Library

Glass slides edged with a coating of teflon 75 microns thick (Fisher "CODE-ON" slides) were coated with "CELL-TAK" (Collaborative Research) following the manufacturer's instructions, rinsed with distilled water, dried for several hours under sterile conditions in a laminar flow hood, and placed into sterile culture dishes.

A human yeast/YAC clone, YAC4, and an untransformed yeast host clone were separately cultured for several days at room temperature in YAC selective medium and in non-selective media, respectively. The freshly cultured log-phase YAC4 recombinant was then diluted into the freshly cultured log-phase host. The dilutions covered a range of 1:100 to 1:1,000,000, YAC4:HOST.

Dilutions were spread on the coated slides in the sterile culture dishes, 1 ml per slide. The 1 ml samples were incubated in contact with each slide for approximately 90 minutes to permit the yeast cells in the sample to gravitate to the surface of the slide and attach to the "CELL-TAK" treated surface. After the incubation period the slides were immersed in YAC selective medium and cultured for 12 hours at room temperature in the sterile culture dishes.

When the slides were examined by microscopy immediately after the initial 90 minute incubation period hundreds of non-selected micro-colonies of 1–4 cells each were seen. These micro-colonies were formed by both YAC4 and untransformed host cells. After 12 hours of growth under YAC-selective conditions, micro-colonies containing several hundred actively dividing cells appeared in a background of apparently moribund micro-colonies containing only a few cells.

The proportion of active and moribund micro-colonies after 12 hours was consistent with the dilution of YAC4 in the host cell background. It was apparent from their ability to grow in YAC-selective medium that the active colonies contained YAC4, while the moribund colonies which were unable to grow apparently corresponded to the untransformed host cell population.

The experiment showed that yeast cells can be reproducibly immobilized on "CELL-TAK" treated surfaces, that libraries of micro-colonies derived from selected cells can be made directly on a "CELL-TAK" treated surface, and that the cells in such colonies remain attached throughout cell division.

"Spiked" Mammalian Micro-Library

To produce a marker cell line for detection in a background of unmarked cells, EMT-6 mouse cells were fused with human U-273 cells transfected with a neo resistance marker and a single neo-resistance EMT-6:human, fused cell-line was isolated. This fusion cell-line was designated HF-10 and was used in the spiking experiments.

EMT-6 cells and HF-10 are attachment dependent cells and were cultured under standard conditions in sterile plastic cultureware. Log-phase cells were recovered using standard trypsin treatment. Dilutions of HF-10 in EMT-6 cells were made at 1:100 to 1:1,000, HF10:EMT-6.

Teflon-edged glass slides (Fisher "CODE-ON" slides) were sterilized as described above and then used without further treatment. The slides were placed in sterile culture plates prior to addition of cells.

One milliliter of a dilution was placed onto each slide and incubated for 90 minutes at 37° C. Some slides were then immersed in selective media while others were immersed in non-selective media. The slides in both types of media were then incubated at 37° C. for several days. Cell growth was periodically examined by microscopy during this period to assess the ability of cells to remain attached to the surface throughout cell division, to assess the effect of growth in selective media, and to assess the general condition of the cells.

Those slides cultured under non-selective conditions produced a confluent layer of contact inhibited cells after approximately five days of growth. The cells appeared morphologically to be quite healthy.

Slides cultured under selective conditions after approximately five days gave rise to many fewer actively dividing cells than companion dilutions grown under non-selective conditions. Selective conditions resulted after five days in relatively isolated micro-colonies consisting on average of 50 to 100 cells. The actively dividing cells of these micro-colonies remained tightly bound to the surface of the slide in the expected manner, forming well defined micro-colonies of healthy, actively dividing neo-resistant cells.

EXAMPLE 2. REPLICATING MICRO-LIBRARIES

Culturing and micro-colony formation was carried out as indicated in EXAMPLE 1 for EMT-6 and HF-10 cells. The cells were cultured from 3 to 8 days until well-formed micro-colonies of approximately 50 to 100 neo-resistant cells appeared in a background of detaching, dying cells.

A slide containing a micro-library was placed face down onto a fresh "CODE-ON" slide prepared for cell growth as described above. To provide a 150 micron gap the 75 micron-thick teflon edges of the two slides were disposed to face each other. Then the slides were placed in a sterilized plastic slide-mailer, which had been selected to maintain the slides tightly in contact at their teflon edges. The mailer containing the slides was then immersed in selective media and cultured 18 to 24 hours at 37° C.

After incubation the slides were separated manually and placed culture side up in fresh sterile petri dishes for further culturing.

Finally, slides were stained to facilitate visualization of micro-colonies (see below). Corresponding, representative visual fields of the slides were compared to assess the fidelity of the replication process. At least 80% of the mother-cell slide micro-colonies were replicated on the daughter-cell slide, and the pattern of micro-colonies in the corresponding visual fields was essentially the same.

EXAMPLE 3. IN SITU SCREENING OF MICRO-COLONIES

EMT-6 cells spiked with HF-10 cells were fixed on slides using the procedures of EXAMPLE 1, and then processed to detect the human/neo DNA marker in micro-colonies of HF-10 cells, as set forth below.

Cells were prepared for hybridization by fixing the cells, removing RNA, and denaturing cellular DNA. Accordingly, slides containing micro-colonies were treated with 70 µl of 100 µg/ml RNase A in 2 X SSC under a coverslip for one hour at 37° C. The slides were then washed in 2 X SSC for approximately two minutes at room temperature. Micro-colonies on the slides were then exposed to proteinase K at 1.0 µg/ml in 20 mM Tris-Cl/2 mM CaCl$_2$/pH 7.5 for five minutes at 37° C. Following proteinase K treatment, cells were dehydrated by successive rinses of approximately two minutes each in 70%, then 85%, and finally 100% ethanol. Slides were covered with 70% (v/v) formamide/2 X SSC, incubated at 72° C. for approximately two minutes to denature DNA, and then quickly quenched and again dehydrated by immersion in ice cold ethanol, using the same concentrations of ethanol and immersion times as previously. The slides were then pre-warmed to 37° C., prior to addition of probe.

A biotinylated µman C$_o$t 1 DNA probe was used to detect by hybridization the small segment of human DNA carried by the neo resistance marker in HF-10 cells. The probe was first biotinylated by random priming. Seventy micoliters of probe mix, consisting of 50% (v/v) formamide/10% (wt/v) dextran sulfate/2 X SSC containing 1.0 µg salmon sperm DNA and 100 ng of biotinylated human C$_o$t 1 DNA, first were incubated for three minutes at 90° C., to denature the DNA, and then were added to the pre-warmed slides which contained the micro-colonies. Hybridization thereafter was carried out overnight in a moist chamber.

Following the hybridization reaction, unbound probe was removed from the slides by a series of washes. Slides were washed for ten minutes twice with 50% (v/v) formamide/2 X SSC at 37° C. The slides were then washed for three minutes at room temperature twice more in 2 X SSC.

Bound biotinylated probe was then detected using fluorescently tagged avidin. The slides were incubated with 70 µl of 1% (w/v) BSA/4X SSC containing 0.5 µg fluorescein-avidin DCS (obtained in this instance from Vector Laboratories) for 30 minutes at 37° C. Following this incubation the slides were washed in 4X SSC /0.05% Tween-20 for three minutes and they were then washed in 4X SSC for three minutes at room temperature.

To improve the signal, an additional amplification step was carried out using a biotinylated anti-avidin antibody as primary reagent and the same fluoresceinated avidin preparation as above to detect binding of the antibody. Thus, slides were incubated with 0.5 µg of biotinylated anti-avidin D (obtained from Vector Laboratories) for 30 minutes at 37° C. Thereafter the slides were washed according to the immediately foregoing wash procedure used after incubation with fluoresceinated-avidin. Then, an additional round of avidin amplification was then carried out using the same procedures, beginning with the fluoresceinated-avidin/BSA incubation step.

Prior to examination to determine binding of the fluorescently label, the slides were treated with 50 µl of 25 µg/ml propidium iodide (in water) to improve visualization of cell nuclei and DNA containing structures.

Finally the slides were examined by visual and fluorescent microscopy. As expected for cells grown in neomycin, all micro-colonies showed strong hybridization to the probe, as evidenced by bright fluorescent signals generated by fluoresceinated-avidin bound to the biotin of the hybridized probe in the cell nuclei.

EXAMPLE 4. SCREENING YEAST/YAC MICRO-LIBRARIES USING FLUORESCENT IN SITU HYBRIDIZATION

Fresh log phase cultures of YAC4-AB1380 and host AB1380 yeast cells were mixed at a ratio of 1:10 YAC4:HOST and grown on slides under selective conditions as described in EXAMPLE 2. The yeast micro-colonies were prepared for hybridization by fixing the cells, removing RNA, and then denaturing DNA, by a method similar to than used with EMT-6 cells. Thus, 50 µl of 100 µg/ml RNase A in 2X SSC was pipetted onto the slide. A coverslip was placed over the solution and the slide was then incubated at 37° C. for one hour in a moist chamber containing 2 X SSC. Following incubation, the slide was washed in 2 X SSC for 3 minutes. The cells on the slide were then dehydrated by immersing the slide first in 70% and then in 95% ethanol for 3 minutes each at room temperature.

DNA in the fixed, dehydrated cells was then denatured by treating the slides with 70% formamide/2 X SSC at 75° C. for 5 minutes. Immediately after the 5-minute incubation, slides were immersed in ice cold 70% ethanol and then in ice cold 95% ethanol for 3 minutes each.

Thereafter cells on the slides were deproteinized by treating each slide with 50 µl of a 6 µg/100 µl solution of proteinase k in 20 mM Tris-HCL/ 2 mM CaCl$_2$, under a coverslip, for 7.5 minutes at 37° C., in a moist chamber. At the end of this period the cells were again dehydrated by immersing the slides successively in 70% and 95% ethanol at room temperature. Finally, the slides were gently dried using an air jet.

Yeast DNA in the cells of the micro-colonies was detected using a biotinylated probe specific for yeast DNA according to a method similar to that described in EXAMPLE 3 FRO probing EMT-6:HL-10 micro-libraries.

The biotinylated probe was prepared by random priming yeast DNA using biotinylated dUTP (obtained from Clonetech). The probe was diluted in distilled, deionized water and denatured by boiling for two minutes and then it was immediately put on ice. 50 µl of denatured, biotinylated probe (at a concentration of 8 ng/µl) was added to each slide, a coverslip was placed over the liquid, and hybridization was allowed to proceed overnight at 37° C., in a moist chamber.

After overnight hybridization, coverslips were removed and slides were washed in 50% formamide/ 2 X SSC at 42° for 10 minutes, twice, using fresh solution each time. The slides were then washed two times with 2 X SSC for 10 minutes at room temperature, again using fresh solution each time. Finally, the slides were washed overnight in 10% NaHCO₃/0.05% NP40 (1X BN buffer) at room temperature.

Biotinylated probe which had bound to DNA in the cells of the micro-colonies was detected using fluorescently labelled avidin, by methods similar to those described above in EXAMPLE 3, as follows. After the overnight wash in 1X BN buffer, slides were coated with 50 μl of a blocking solution which contained 10% nonfat milk in 0.2 mg/ml NaN₃/10% NaHCO₃/0.05% NP40 (1X BNN) for 5 minutes at room temperature. The slides were then incubated in a solution containing 5 μg/ml final concentration fluorescein-avidin-DCS in 10% non-fat dry milk in 1X BNN for 30 minutes at 37° C. in a moist chamber containing 1X BN buffer. At the end of 30 minutes the slides were washed twice with 1 X BN buffer at 42° C. for three minutes each wash.

Slides were then incubated with a solution containing 2.5% 500 μg/ml biotinylated anti-avidin DCS (Vector Laboratories) for 30 minutes at 37° C. in a moist chamber. After incubation the slides were washed twice with 1X BN buffer at 42° for 3 minutes each wash, to remove unbound anti-avidin. The avidin binding and wash procedures were then repeated exactly as before, with an additional, final wash in 1X BN buffer for 10 minutes at room temperature.

20 μl of anti-fading solution (90% v/v glycerol/1 mg/ml p-phenylenediamine dihydrochloride/10% phosphate buffered saline) was then applied to each slide, under a cover slip, to prevent quenching.

In addition to slides containing micro-colonies grown from log-phase YAC4 cells diluted 1:10 in log phase host cells, control slides were made using the same procedures except for the differences noted below.

In one set of control slides, a 1:100 dilution of YAC4 into AB1380 host cells was used, and the entire procedure was carried out as before except for the omission of probe from the probe hybridization step.

In the second set of control slides, all the preceding procedures were the same except that yeast DNA that had not been biotinylated was used in place of the biotinylated probe.

In all the experiments, individual YAC containing microcolonies grown under selection conditions showed bright fluorescence ue to binding of the yeast DNA probe, apparently to yeast nuclear DNA. Some cells showed doubly bright fluorescent staining, probably indicating dividing yeast cells. No staining of nuclear regions of yeast cells in the micro-colonies was observed in the control experiments that were performed, i.e., without adding a probe, or using as probe yeast DNA that had not been biotinylated. Thus, labelling was associated with hybridization of biotinylated probe to complementary DNA in situ. In sum, the staining patterns that were observed are consistent with specific hybridization of biotinylated probe to yeast nuclear DNA, and they demonstrate that in situ hybridization procedures than are well known in the art can be used to detect DNA elements in yeast cells in micro-colonies.

What is claimed is:

1. Micro-libraries for identifying a sub-population in a library, comprising:
   (A) a first micro-library that is a replicate of an original micro-library and comprises a plurality of spatially distinct, microscopic sub-populations immobilized on a first surface, wherein each of said sub-populations is formed from clonally derived cells, substantially every sub-population is formed from between 1 and 1,000,000 cells and the approximate density of said sub-populations on said surface is between 10 sub-populations per mm² and 10⁶ sub-populations per mm², and
   (B) a second micro-library immobilized on a second surface, wherein said second micro-library is the original micro-library or a replicate of the original micro-library, and wherein the sub-populations of said second micro-library are positioned on said second surface in a spatial relationship with respect to one another which is substantially similar to the spatial relationship with respect to one another of the sub-populations of said first micro-library on said first surface, such that corresponding sub-populations in said first and second micro-libraries can be identified by their similar positions in said spatial relationships on said first and second surfaces.

2. Micro-libraries according to claim 1, for identifying a DNA in a cDNA or genomic library, wherein each of said sub-populations contains exogenous DNA and said exogenous DNA is the same in the cells forming a given sub-population.

3. Micro-libraries according to claim 1, wherein the sub-populations of said micro-libraries are positioned on said surfaces in a random spatial relationship with respect to one another.

4. Micro-libraries according to claim 1, wherein the sub-populations of said micro-libraries are positioned on said surfaces in a predetermined spatial relationship with respect to one another.

5. Micro-libraries according to claim 1, wherein cells of the sub-populations on said second surface are viable cells and said second surface is for storing viably or culturing said cells.

6. Micro-libraries according to claim 1, wherein said micro-libraries consist of bacterial, yeast, insect, plant or mammalian cells.

7. Micro-libraries according to claim 1, wherein said micro-libraries consist of bacterial or yeast cells.

8. Micro-libraries according to claim 2, wherein said cDNA or genomic library is a mammalian cDNA or genomic library.

9. Micro-libraries according to claim 8, wherein said genomic or cDNA library is a human genomic library or a human cDNA library.

10. Micro-libraries according to claim 8, wherein said genomic or cDNA library is a YAC genomic library.

11. Micro-libraries according to claim 10, wherein said YAC genomic library is a YAC human genomic library.

12. A plurality of replicate micro-libraries of clonally derived sub-populations, wherein:
   (A) each micro-library of said plurality is a clonally-derived replicate of a common, original micro-library;
   (B) each micro-library consists of a multiplicity of spatially distinct microscopic sub-populations immobilized on a surface and each of said sub-populations is formed from clonally derived cells;
   (C) said sub-populations are positioned in each of said micro-libraries in substantially the same spatial relationship with respect to one another, such that a given sub-population occupies, in each of said micro-libraries, substantially the same position in relation to other sub-populations;
   (D) substantially every sub-population is formed from between 1 and 1,000,000 cells and the approximate density of said sub-populations on said surface is between 10 sub-populations per mm² and 10⁶ sub-populations per mm², and
   (E) sub-populations in said micro-libraries differ in at least one genotypic characteristic.

13. A plurality of replicate micro-libraries according to claim 12, wherein said micro-libraries consist of bacterial, yeast, insect, plant or mammalian cells.

14. A plurality of replicate micro-libraries according to claim 12, wherein each of said micro-libraries is a genomic library or a cDNA library.

15. A plurality of replicate micro-libraries according to claim 14, wherein said genomic library is a YAC genomic library.

16. A plurality of replicate micro-libraries according to claim 14, wherein said genomic or cDNA library is a human genomic library or a human cDNA library.

17. A plurality of replicate micro-libraries according to claim 15, wherein said human genomic library is a YAC human genomic library.

18. A plurality of replicate micro-libraries of clonally derived sub-populations, wherein:

(A) each micro-library of said plurality is a clonally-derived replicate of a common, original micro-library;

(B) each micro-library consists of a multiplicity of spatially distinct microscopic sub-populations immobilized on a surface and each of said sub-populations is formed by clonally derived cells;

(C) said sub-populations are positioned in each of said micro-libraries in substantially the same spatial relationship with respect to one another, such that a given sub-population occupies, in each of said micro-libraries, substantially the same position in relation to other sub-populations;

(D) substantially every sub-population is formed from between 1 and 1,000,000 cells and the approximate density of said sub-populations on said surface is between sub-populations per $mm^2$ and $10^6$ sub-populations per $mm^2$;

(E) sub-populations in said micro-libraries differ in at least one genotypic characteristic, and (F) said micro-libraries are made by a process comprising the steps of:

(a) forming the original micro-library by providing a population I of cells that represents a plurality of sub-populations that differ, one from another, by at least one genetic characteristic and immobilizing said population I on a surface I such that said cells are retained, the approximate density of said sub-populations is between 10 sub-populations per $mm^2$ and $10^6$ sub-populations per $mm^2$ and substantially every sub-population is formed from between 1 and 1,000,000 cells; then (b) forming a replicate micro-library by bringing said surface I into close proximity of a surface II such that:

(i) daughter cells replicated from cells on said surface I, but not cells of said population I, come into contact with and are immobilized on said surface II during the process of replication or after separating from said cells on said surface I, and (ii) sub-populations of said daughter cells immobilized on said surface II are positioned thereon in a spatial relationship with respect to one another which is substantially similar to the spatial relationship with respect to one another of said sub-populations of said population I immobilized on said surface I.

* * * * *